(12) United States Patent
Johnnie et al.

(10) Patent No.: US 8,911,891 B2
(45) Date of Patent: Dec. 16, 2014

(54) BATTERY ELECTROLYTE LEVEL DETECTOR APPARATUS

(75) Inventors: Nathan Johnnie, Middletown, RI (US); Francis J. O'Brien, Jr., Newport, RI (US); Helene B. Anderson, West Greenwich, RI (US); Joseph W. Robicheau, Portsmouth, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 703 days.

(21) Appl. No.: 12/693,708

(22) Filed: Jan. 26, 2010

(65) Prior Publication Data

US 2011/0183168 A1 Jul. 28, 2011

(51) Int. Cl.
*H01M 10/48* (2006.01)
*G01F 23/28* (2006.01)
*G01F 23/296* (2006.01)

(52) U.S. Cl.
CPC ........... *H01M 10/484* (2013.01); *G01F 23/296* (2013.01); *G01N 2291/02836* (2013.01)
USPC .......................................... 429/93; 73/290 V

(58) Field of Classification Search
USPC ............................................ 429/93; 73/290 V
See application file for complete search history.

(56) References Cited

U.S. PATENT DOCUMENTS

| 4,315,301 | A | * | 2/1982 | Jimena | 362/193 |
| 4,329,406 | A | * | 5/1982 | Dahl et al. | 429/92 |
| RE31,607 | E | * | 6/1984 | Vogel et al. | 367/86 |
| 4,605,304 | A | * | 8/1986 | Leitz et al. | 356/138 |
| 7,246,522 | B1 | * | 7/2007 | Diaz et al. | 73/597 |

* cited by examiner

*Primary Examiner* — Gregg Cantelmo
(74) *Attorney, Agent, or Firm* — James M. Kasischke; Michael P. Stanley

(57) ABSTRACT

An electrolyte detector is provided that includes two micrometers which slide relative to each other along a frame to adjust the electrolyte detector to a size of the battery. A transmitter rod and a receiver rod support an acoustic transmitter and an acoustic receiver, respectively, and are slidably mounted with respect to the micrometers. The micrometers measure the position of the transmitter and receiver for placement on the side of the battery at a desired level of electrolyte. A transmitter director and receiver director concentrates the transmission and receipt of acoustic energy to locate the electrolyte level. An electronic circuit analyzes the received signal to determine whether the signal is transmitted through air or through an electrolyte.

1 Claim, 5 Drawing Sheets

BATTERY ELECTROLYTE LEVEL DETECTOR APPARATUS

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

None.

BACKGROUND OF THE INVENTION

1. Field of the Invention

The present invention relates generally to battery electrolyte level testing and, more particularly, to an external apparatus and methods to check battery electrolyte levels.

2. Description of the Prior Art

It is well known that a wide variety of machines, vehicles, and the like, utilize batteries with electrolyte levels that need to be periodically checked. In lead-acid batteries, during normal operation, sulfuric acid is not lost from the electrolyte of the battery. However, water is lost from the electrolyte due to evaporation and electrolysis during ventilation and charge operations.

The water needs to be replaced regularly to ensure that the electrolyte remains at a proper level. The required frequency for adding water may be determined by maintaining a close watch of electrolyte levels. If the battery electrolyte level is too low, the battery may be permanently damaged. When necessary, and if practical, water should be added before a charge operation, preferably before an equalizer. This procedure allows the water to mix with the electrolyte during the charge.

Checking the water level on batteries is time-consuming and potentially dangerous due to the need to open the battery caps, and look into the cells to see the level. Sulfuric acid fumes inhalation, spillage, explosions due to hydrogen production, and skin contact with acid are real dangers faced by sailors testing the water level on batteries.

The following United States patents describe various prior art systems that may be related to the above and/or other problems.

U.S. Pat. No. 4,280,126, issued Jul. 21, 1981, to White discloses an apparatus for locating the level of a liquid in a closed metallic container having curvilinear walls with a thickness of from ⅛ to ⅜ inch comprising a manually portable transducer having a piezoelectric material for transmitting and receiving sonic waves, and a sonic pulse generator capable of exciting the piezoelectric material to emit sonic signals into the container from a location adjacent the outside wall of such container at a frequency within about 20% of the natural resonate frequency of the container. The apparatus further includes the electronic circuitry necessary for determining that the reception of the sonic signals transmitted into the container is in balance when the transducer is at a location away from the interface of the fluids within the container, and the electronic circuitry necessary for determining the vertical location at which the reception of sonic signals transmitted into the container is no longer balanced as the transducer is manually moved toward the interface of the fluids.

U.S. Pat. No. 5,017,909, issued to May 21, 1991, to Goekler discloses a non-intrusive fluid level detector including a single point capacitive sensor mounted on the outside surface of a receptacle such that capacitive principles can be utilized to sense the level of a liquid contained within the receptacle. The sensor assembly is disposed in a substantially fixed position on the exterior wall of the receptacle wherein the dielectric effect of the liquid changes the effective capacitance of the sensing capacitor as the liquid rises and falls within the receptacle. This change in effective capacitance is detected by electronic circuitry included in the detector device. In one embodiment, the fluid level detector is directly mounted to a completely non-conductive receptacle. In another embodiment, the fluid level detector is mounted to a non-conductive window which is an integral part of a receptacle fabricated out of a conductive material.

U.S. Pat. No. 5,132,626, issued Jul. 21, 1992, to Limuti et al, discloses nonintrusive sensors capable of measuring various storage cell parameters such as voltage, state-of-charge, electrolyte level, internal resistance, and temperature are attached to a monitoring module which gathers and processes signals representative of information concerning the condition of electrolytic storage cells and transmits the information to a central computer for further processing. In response to commands issued by the central computer, appropriate maintenance and/or repair operations can be initiated. Alternatively, the system described can be used to automatically perform such maintenance tasks as checking and adding electrolyte levels, reducing the voltage in cells whose output voltage is too high, and leveling the state-of-charge of each cell in an array of electrolytic storage cells. The system can monitor other functions of the electrolytic storage cells, including the evolution of hydrogen gas and the accumulation of sediments in individual electrolytic storage cells.

U.S. Pat. No. 5,438,868, issued Aug. 8, 1995, to Holden et al, discloses a noninvasive ultrasonic liquid level indicator for indicating the level of a liquid in a reservoir which comprises an ultrasonic transducer assembly, structures for holding the transducer assembly in a dry coupled attachment with the reservoir at selectable locations against an exterior surface of the reservoir, and a monitor for revealing a change in liquid height. The transducer assembly conveys signals regarding changes in liquid height to a monitor which warns the user in time to add more liquid or replace the reservoir before the liquid supply "runs dry." The manners for holding the assembly in place include, but are not limited to, a strap, a clamp, or adhesive material, such as tape. These manners allow the user to selectively place the transducer assembly along the reservoir at the desired triggering point.

U.S. Pat. No. 5,880,364, issued Mar. 9, 1999, to Dam discloses a non-contact ultrasonic system for measuring the volume of liquid in a container in which an ultrasonic sensor is disposed opposite the top of the container. A circuit provides pulses of ultrasonic energy for transmission through the air to the air-liquid interface of liquid in the container and for measuring the round trip transit time from the sensor to the interface and back to the sensor. A computer is programmed with dimensional data of the container internal volume and computes the volume of liquid in the container based on the dimensional data and the round trip transit time. The computed volume data is stored. The system can measure the volume of a plurality of containers using a plurality of sensors that are operated in sequence or at the same time or single sensor in which the plurality of sensors are moved relative to the single sensor for the volume of each of the sensors to be sequentially measured.

U.S. Pat. No. 6,227,053, issued May 8, 2001, to Purpura et al, discloses a sensor that emits a plurality of ultrasonic bursts. A rack of containers is transported under the sensor at a slew speed that allows the sensor to detect at least first and second echoes from each of the bursts. Data points, corresponding to each of the first and second echoes, are generated and the data points are captured in a memory device. The data points, generally reflecting the levels of the rack and any containers, are processed to dynamically and non-invasively (i.e., without physically contacting the liquid with a probe) determine information about the container types, whether any container is capped, and, if one or more containers are uncapped, the liquid level in the uncapped containers. This profiling may be used in a variety of devices and is particularly useful in a sample handler in an automated analytical instrument, where the ultrasonic sensor may be positioned above a rack transport mechanism.

U.S. Pat. No. 6,943,566, issued Sep. 13, 2005, to Florin et al, discloses a sensor which is applied to the wall of a container or is integrated into the wall. An alternating voltage is applied to the sensor in order to measure the level of the contents of the container, the capacitance or the electrical field produced being a measure for the fill level.

United States Patent Publication No. 2002/0083766, published Jul. 4, 2002, for Hongerholt et al, discloses a built-in test system for an ultrasonic liquid level sensor that includes a transducer assembly having an ultrasonic transducer, and a switch that will be actuated when the ultrasonic transducer is in intimate contact with a surface of a tank in which level is to be determined. Once the switch is actuated to indicate that the ultrasonic transducer is properly coupled to the surface, a test sequence is initiated to determine that the level of ultrasonic transmissions are above a certain desired threshold for a selected period of time, and after which the circuit looks for echoes to determine the depth of the liquid in the tank. Thereafter, the test sequence is repeated for each cycle of level sensing.

United States Patent Publication No. 2001/0015099, published Aug. 23, 2001, for Blaine, discloses a disposable sensor for non-invasively detecting and characterizing a container's contents. By generating microwave frequency signals, electromagnetic fields are produced by a sensor and penetrate a container. The EM fields are analyzed in regards to how they are perturbed by the container contents. Analysis of the perturbed EM fields enables determination of content level, content purity, content density, content temperature, container pressure, content conductivity, and the like.

U.S. Patent Publication No. 2007/0261487, published Nov. 15, 2007, for Sintes et al, discloses a level sensor for providing an indication of liquid level in a container comprising: an ultrasonic transducer for emitting an ultrasonic signal to the surface of the liquid and for detecting a return signal, reflected from the surface, a controller that instructs the transducer to emit ultrasonic signals and receives an indication that a return signal has been detected, the controller comprising a timer for measuring the time period between emission of the ultrasonic signal and receipt of a return signal, the determined time period providing an indication of the liquid level, and a radio transmitter that receives an indication of the liquid level and transmits a radio liquid level signal comprising the level indication to a remote output unit.

Extract from Japanese Patent No. 2000-5636041, discloses a supersonic sensor that is made to contact the outer surface of battery case. An ultrasonic wave is transmitted towards a battery case from an ultrasonic element of sensor. The magnitude of ultrasonic wave reflected from an inner surface of battery case is detected to judge liquid level inside battery case.

Extract from Japanese Patent No. 2000-205931, discloses a method to inspect the liquid level of a battery liquid by setting the size of an inside surface reflected wave generated in the first place on a boundary surface existing on an inside surface of a battery case as an evaluation index.

The above cited prior art does not disclose a suitable and transportable means to acoustically check battery electrolyte levels with micrometer accuracy without opening the cell caps. Consequently, those skilled in the art will appreciate the present invention that addresses the above and other problems.

SUMMARY OF THE INVENTION

It is a general purpose and primary object of the present invention to provide an improved apparatus and method for checking the electrolyte level in a battery.

It is a further object of the present invention to provide a safer and more efficient means for checking the electrolyte level in a battery.

It is a still further object of the present invention to provide a non-intrusive apparatus and method of checking the electrolyte level to reduce the need to open the caps on the battery.

Accordingly, the present invention provides an apparatus for externally checking a level of electrolyte within a battery. The apparatus may comprise elements such as a frame which is engageable with the battery, and a first and second micrometer carried by the frame. The first micrometer and second micrometers may slide along the frame with respect to each other to adjust to a size of the battery.

Other elements of the detector may comprise an acoustic transmitter supported on a transmitter rod. The transmitter rod may be slidably mounted with respect to the first micrometer so that the first micrometer is operable to measure a position of the slidable transmitter rod for placement of the acoustic transmitter adjacent to a desired level of electrolyte within the battery.

Similarly, an acoustic receiver is supported on a receiver rod. The receiver rod is slidably mounted with respect to the second micrometer so that the second micrometer is operable to measure a position of the slidable receiver rod for placement of the acoustic receiver adjacent the desired level of an electrolyte within the battery.

Electronic receiver circuitry is operable to distinguish between an acoustic signal that passes through air indicating a low level of electrolyte within the battery and an acoustic signal that passes through fluid indicating a satisfactory level of electrolyte within the battery.

In one embodiment, the electronic receiver circuitry may comprise a first band pass filter and a second band pass filter operably connected to the acoustic receiver. The first band pass filter is operable for passing an electrical signal indicative of a satisfactory level of the electrolyte within the battery. The second band pass filter is be operable for passing an electrical signal indicative of a low level of electrolyte within the battery.

The apparatus may further comprise an acoustic transmitter director for directing acoustic transmitter energy. The transmitter director may comprise a first transmitter socket cup positioned adjacent to a second transmitter socket cup. The apparatus may further comprise an acoustic receiver director for the acoustic receiver. The acoustic receiver director may comprise a first receiver socket cup positioned adjacent to a second receiver socket cup.

The first transmitter socket cup may be larger in size than the second transmitter socket cup and the first receiver socket cup may be larger in size than the second receiver cup. The second transmitter socket cup and the second receiver socket cup may be positioned for contacting the battery.

The first micrometer and the second micrometer may be pivotally mounted to the frame for stowage of the electrolyte level detector in a compact position. The apparatus may further comprise a handle connectable to the transmitter rod and the receiver rod operable for simultaneous movement of the transmitter rod and the receiver rod.

The invention also provides a method for making an electrolyte level detector for externally checking a level of electrolyte within a battery. The method may comprise steps such as mounting a first micrometer on a frame, mounting a second micrometer to the frame, and providing that at least one of the first micrometer or the second micrometer is slidable along the frame for adjusting to a size of the battery.

Other steps may comprise supporting an acoustic transmitter on a transmitter rod, slidably mounting the transmitter rod with respect to the first micrometer, and providing that the first micrometer is operable to measure a position of the slidable transmitter rod for placement of the acoustic transmitter adjacent a desired level of electrolyte within the battery.

The method may further comprise supporting an acoustic receiver on a receiver rod, slidably mounting the receiver rod with respect to the second micrometer, and providing that the second micrometer is operable to measure a position of the slidable receiver rod for placement of the acoustic receiver adjacent the desired level of electrolyte within the battery.

Other steps may comprise providing an acoustic transmitter director for the acoustic transmitter, which may comprise a first transmitter socket cup positioned adjacent to a second transmitter socket cup. The method may further comprise providing an acoustic receiver director for the acoustic receiver, which may comprise a first receiver socket cup positioned adjacent to a second receiver socket cup.

The method may further comprise providing a first band-pass filter and a second band-pass filter operably-connected to the acoustic receiver wherein the first band-pass filter is operable for passing an electrical signal indicative of a satisfactory level of the electrolyte within the battery and the second band pass filter is operable for passing an electrical signal indicative of a low level of the electrolyte within the battery.

The method may further comprise providing that the acoustic transmitter director and the acoustic receiver director are comprised of soft plastic material. Also, the method may further comprise filling the first transmitter socket cup and the first receiver socket cup with acoustic couplant.

The method may further comprise providing that the first transmitter socket cup is larger in size than the second transmitter socket cup and/or the first receiver socket cup is larger in size than the second receiver cup. The method may further comprise pivotally mounting the first micrometer and the second micrometer to the frame for compact storage of the electrolyte level detector.

The method may further comprise connecting a handle to the transmitter rod and the receiver rod to provide for simultaneous movement of the transmitter rod and the receiver rod.

The present invention may be utilized to enhance efficiency, accuracy, and safety of battery maintenance for many machines, vessels, and vehicles including, for example, naval submarines, surface ships, and other military, private, surface, and/or submersible vessels. Accordingly, the present invention has utility for a wide variety of military and civilian batteries including but not limited to secondary batteries, wet cells, water-based batteries, lead-acid batteries and rechargeable batteries.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings, wherein like reference numerals refer to like parts and wherein.

DETAILED DESCRIPTION OF THE INVENTION

Figure 1:
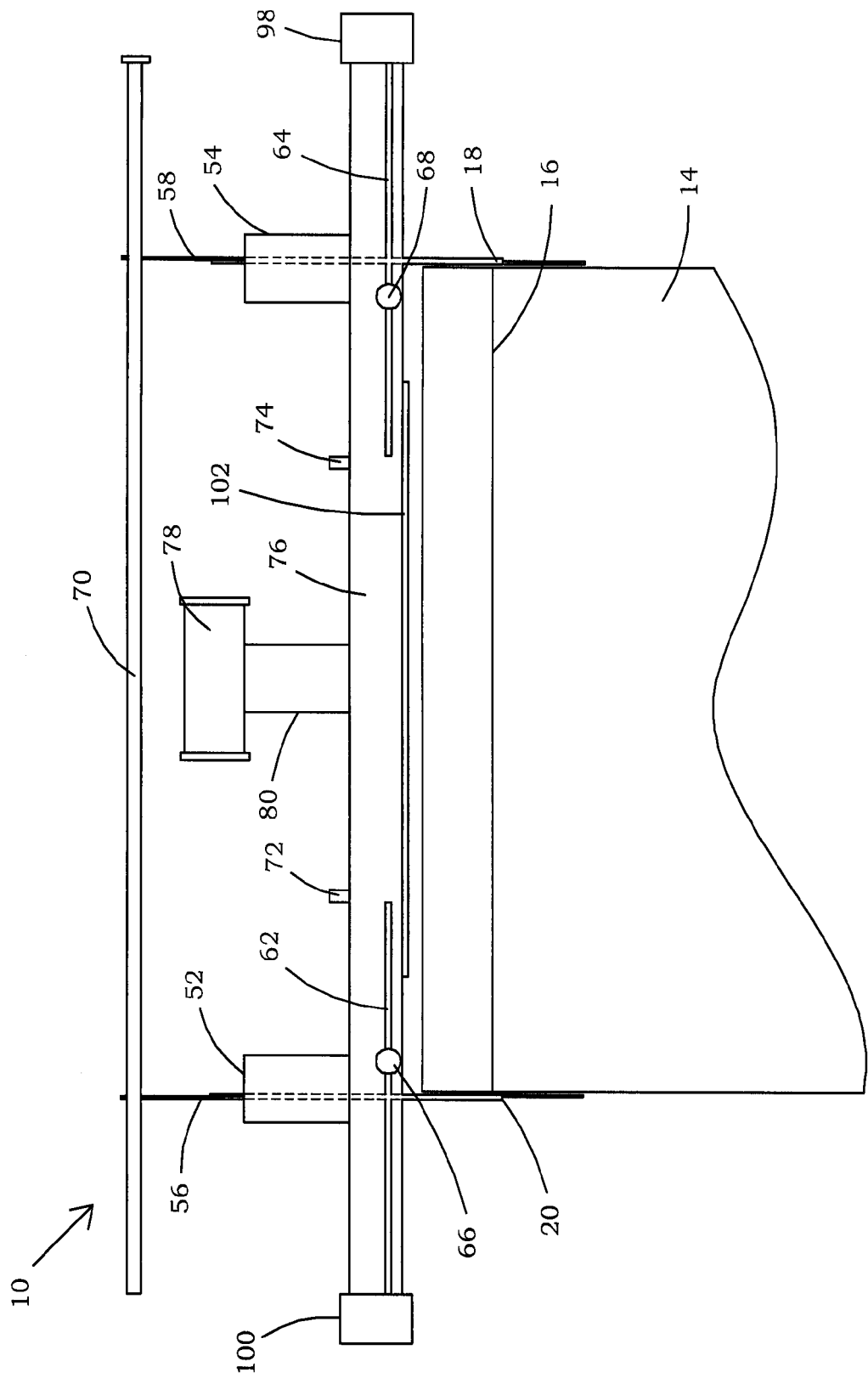
FIG. 1 is an elevational view, partially in dashed lines, which shows a battery electrolyte level detector mounted across a pilot cell of a battery in accordance with one embodiment of the present invention.
Figure 2:
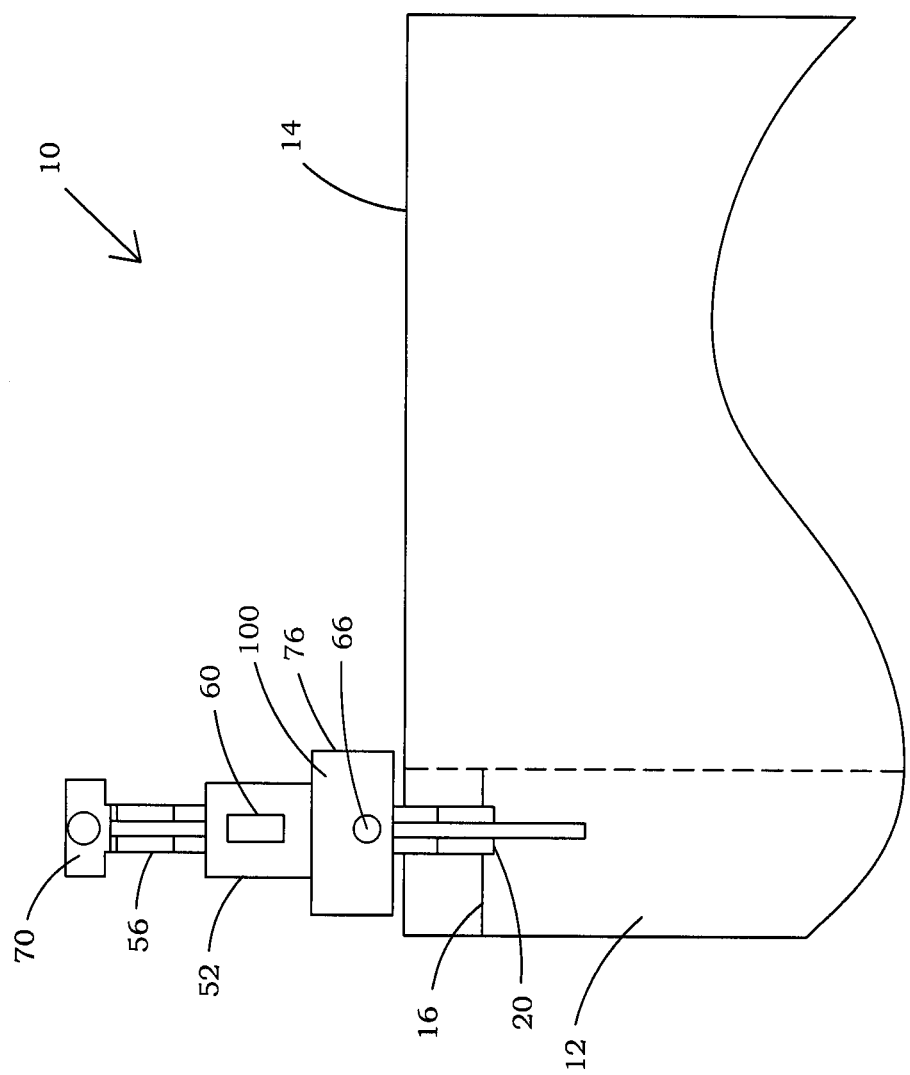
FIG. 2 is an elevational view of the battery electrolyte level detector of FIG. 1 wherein the battery is shown in a front view in accord with one possible embodiment of the present invention.

Referring now to the drawings and, more particularly to FIG. 1 and FIG. 2, there is shown an electrolyte level detector 10 mounted on across a cell 12 of a battery 14. The level detector 10 can determine whether the battery 14 has lost water due to evaporation and/or electrolysis by checking a battery electrolyte level 16.

Figure 5:
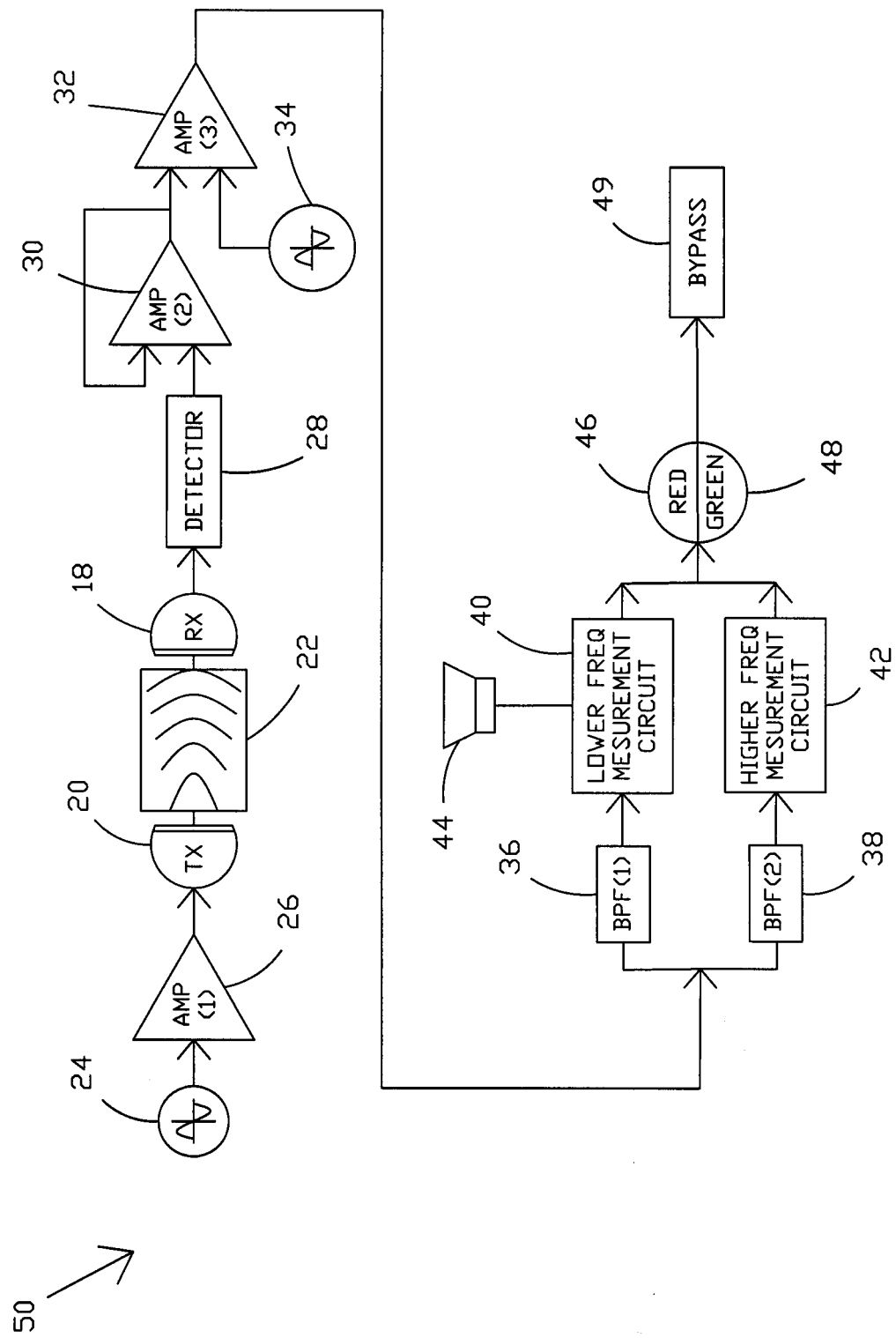
FIG. 5 is a functional block diagram for a battery electrolyte level detector in accordance with the present invention.

FIG. 5 depicts electronic functional elements 50 of the level detector 10. These elements include an acoustic receiver 18 and a transmitter 20 which transmits an acoustic signal through a medium 22, which may be either air or an electrolyte within the battery 14. A wave generator 24 produces a signal to be transmitted, which is amplified by an amplifier 26 and transmitted by the transmitter 20 through the battery wall into the medium 22. The receiver 18 receives the signal from the medium 22 through the battery wall.

In this embodiment, a frequency differentiator section is utilized to determine whether the sound waves traveled through air or water. However, various circuits, known to those skilled in the art, may be utilized to analyze frequencies, speed, and/or wavelength to determine whether the signal traveled through air or a fluid medium.

A detector 28 and an amplifier 30 produce an electrical signal from sound waves and then amplify the detected signal. A sinusoidal signal may be produced by a generator 34 and added to the detected signal in an amplifier 32 to convert the signal to a pulse width modulation signal. The pulse width modulation signal is applied to two band pass filters 36 and 38, which block unwanted signals and noise but pass either lower frequency signals or higher frequency signals.

Lower frequency signals pass through the band pass filter 36 and are detected at circuit 40. The circuit 40 drives visual or auditory indicators that warn the operator that the acoustic signal traveled through air, which is indicative of a low level of electrolyte. The speed of sound in air is about 342 meters per second depending on ambient temperature. When the circuit 40 recognizes that the signal passed through air, then the circuit may activate an alarm such as piezoelectric speaker 44 and/or red LED 46.

Higher frequency signals are detected at a circuit 42 after passing through the band pass filter 38. The speed of sound is water is approximately 1500 meters per second depending on ambient temperature. The circuit 42 recognizes that the waveform signal passes through water and may activate a green LED 48 or any other desired indicator to indicate that the electrolyte level is acceptable. With that in mind, and referring again to FIG. 1 and FIG. 2, the acoustic receiver 18 and the acoustic transmitter 20 are positioned on the sides of the battery 14 at or just below the desired electrolyte level. The acoustic receiver 18 and the acoustic transmitter 20 may be adjusted to a precise level at the sides of the battery 14 by utilizing micrometers 52 and 54. The micrometers 52 and 54 may be constructed in various ways and may comprise commercially-available micrometers.

Transmitter support rod 56 and receiver support rod 58 carry the transmitter 20 and the receiver 18, respectively. The transmitter support rod 56 and the receiver support rod 58 are slidable up and down to thereby position the transmitter 20 and the receiver 18 at the desired height on the case of the battery 14 relevant to electrolyte level 16 within the battery 14. In one embodiment, electronic micrometer readouts are utilized such as electronic readout 60 (see FIG. 2) for the transmitter rod 56. However, scales or the like may be inscribed on the transmitter rod 56 and the receiver rod 58 for manual micrometer measurements.

The micrometers 52 and 54 are preferably coated with non-conductive material so as to avoid shock hazards. The micrometers 52 and 54 are preferably slidably-mounted for movement on pins 66 and 68 in slots 62 and 64 along rail members 76 to adjust to different size battery casings. Once the micrometers are placed at the correct position in the slots 62 and 64; knobs or tightening means may be utilized with the pins 66 and 68 to threadably tighten or otherwise affix the micrometers at the desired position. End retainers 98 and 100 may be utilized to secure the rail members 76. If desired, bottom plate member 102 may be utilized to adapt to particular battery shapes and/or provide additional support.

The micrometers 52 and 54 may also be pivotally mounted on the pins 66 and 68, for stowing once an adjustment arm 70 is removed. For example, once the adjustment arm 70 is removed, and the electrolyte level detector 10 is removed from the battery 14, then the micrometers 52 and 54 may be mounted to pivot on the pins 66 and 68 along the rail members 76 to a position parallel with the rail members to provide a compact electrolyte level detector in a stowed position.

The adjustment arm 70 may be utilized to simultaneously move the transmitter support rod 56 and the receiver support rod 58 up and down. The user can check the micrometer readouts to verify that both the transmitter 20 and the receiver 18 are at the correct levels.

The desired electrolyte level for each battery type is assumed to be known. In many batteries, it may only be necessary to measure the electrolyte level at pilot cells, which may typically be on the ends of the battery. The adjustment arm 70 may be removable for stowing the electrolyte level detector 10. In this case, rod holders 72 and 74 may be designed to snap-fit onto the adjustment arm 70 for stowage after the micrometers 52 and 54 are pivoted to the stowed position, as discussed above.

Grip 78 may be utilized to carry the electrolyte level detector. The batteries for electronic circuit operation may be mounted in the grip 78 and the electronics housed in cylinder 80. The grip 78 may be removable. The LEDs 46 and 48 (shown in FIG. 5) and/or the piezoelectric speaker 44 may also be mounted in the grip 78 or the cylinder 80.

Figure 3:
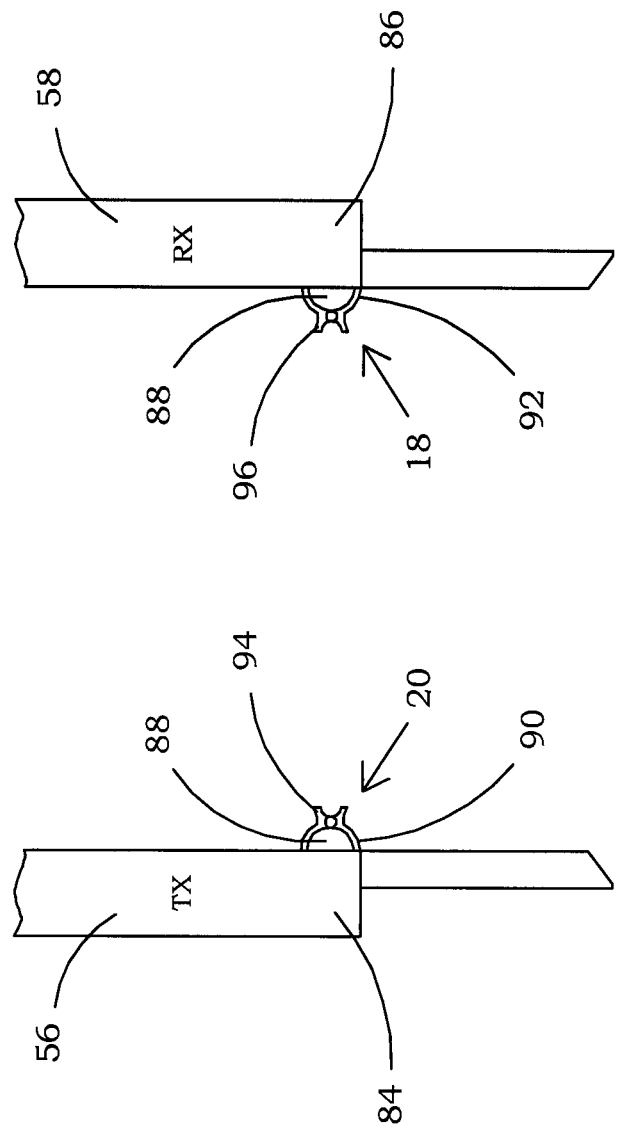
FIG. 3 is an enlarged elevational view of acoustic transmitter and receiver directivity control elements in accordance with one embodiment of the present invention.

FIG. 3 depicts an enlarged view of a preferred transmitter 20 and receiver 18. In this embodiment, suitable piezoelectric elements may be positioned along the transmitter support rod 56 and the receiver support rod 58 at positions 84 and 86 in which the piezoelectric elements produce and/or receive acoustic energy.

In this embodiment, relatively larger socket cups 90 and 92 adjacently connected to relatively smaller socket cups 94 and 96, respectively, comprise soft plastic material to thereby form acoustic directors. The acoustic directors direct or concentrate the acoustic energy over a relatively small point of contact with the battery 14 for a more precise determination of the location of the electrolyte level. The soft plastic material tends to deaden transmission except through the larger and smaller socket cups. Harder material may be positioned at the contact region between the larger and smaller socket cups to enhance acoustic transmission therebetween. Thus, acoustic energy over the larger area of the relatively larger transmitter socket cup 90 is transferred to a smaller region in the relatively smaller socket cup 94.

Acoustic couplant such as jelly or other acoustically conductive material 88 may be positioned in the relatively larger socket cups 90 and 92. The relatively smaller socket cups 94 and 96 may be filled with jelly or other acoustically conductive material including water for contact with the battery wall at the time of testing. Various types of acoustic couplant materials are commercially-available for this purpose. This acoustic couplant jelly-like material may be added prior to measurement and/or may be contained within a membrane.

The socket cups 90 and 92 have an additional function in that they act as pin-point directors of acoustic energy to more precisely determine the level of the electrolyte. All or most of the acoustic energy is transmitted and received through the socket cups 94 and 96. The socket cups 94 and 96 are preferably less than one-quarter inch in diameter and may be less than one-eighth of an inch in diameter. Thus, the level of the electrolyte is determinable within less than one-quarter inch or less than one-eighth inch.

Figure 4:
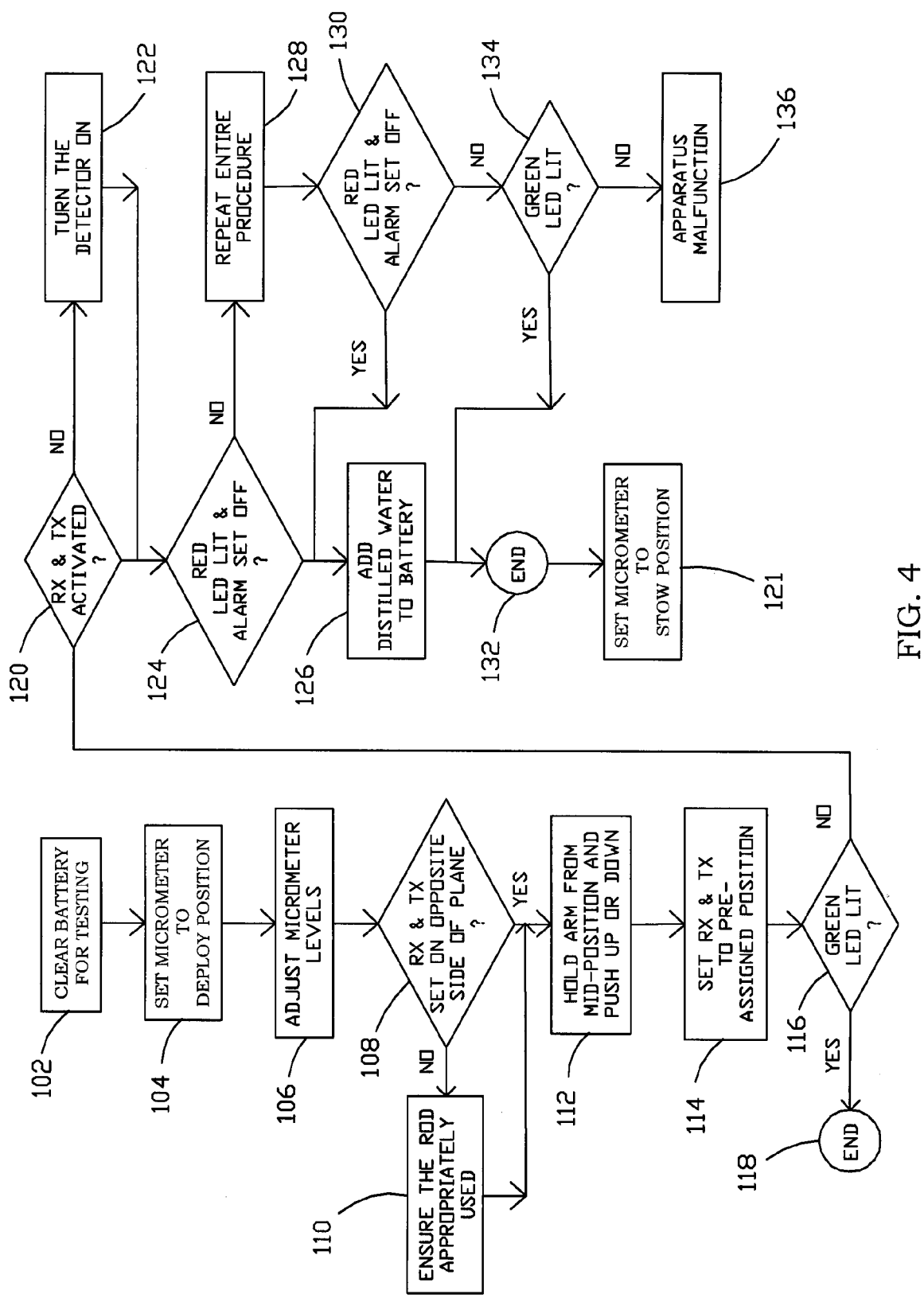
FIG. 4 is a flowchart for operation of a battery electrolyte level detector in accordance with one possible embodiment of the present invention.

FIG. 4 shows steps that may be utilized during operation. As indicated at step 102, the battery 14 may be cleared off or wiped down or cleaned on the outer surfaces for testing. At step 104, the micrometers 52 and 54 are placed in a vertical position and spaced apart in the slots 62 and 64 to fit onto the battery 14. Knobs, such as the knobs 66 and 68 are tightened, to secure the micrometers 52 and 54 in the desired position in the slots 62 and 64 along the rails 76.

At step 106, an adjustment arm 70 may be utilized to simultaneously move the transmitter support rod 56 and the receiver support rod 58 up and down so that the transmitter 20 and receiver 18 are level with each other according to the micrometers. At 108 and step 110, the operator insures that electrolyte level detector 10 is inserted over the battery 14 at the correct position for checking the electrolyte level of a selected cell.

At steps 112 and 114, the arm 70 is utilized to adjust the transmitter 20 and the receiver 18 up and down to the pre-assigned position.

At step 116, if the green LED lights up, then the battery check is completed as indicated at step 118. If desired, the electrolyte level detector 10 can then be set to the stowed position as indicated at step 121 by pivoting the micrometers to a position which is level with rails 76 (See FIG. 2).

If the green light does not come on, then steps 120 and 122 are used to verify that the transmitter and receiver are activated, such as by checking the on-off switch. If the red light comes on at 124, then water is added at step 126. If the red light is not on, then the procedure is repeated—as indicated at step 128. If the red light comes on, as indicated at 130, then water is added to the battery as indicated at step 126. If the green light comes on as per 134, then the test is ended as indicated at 132. If at this time, neither the red light nor the green light is on, then there may possibly be a malfunction as indicated at step 136. This requires checking on procedures, acoustic coupling, the circuitry In FIG. 1 (a bypass switch 49 is provided to ensure that any electrical equipment such as batteries or the LED 46 and 48 are operating properly), and the like. Steps of adding electrolyte may be repeated as necessary until the green light comes on. Because the battery level can be quickly checked without opening the battery in many cases, the present invention provides a safer and faster way of checking electrolyte levels.

It will be understood that the electrolyte level detector 10 can be modified in various ways. For example, in one possible embodiment, the number of acoustic sensors may be increased, such as by utilizing a wiring harness. The circuitry for the acoustic sensors may be connected to a central computer processor to analyze and monitor multiple batteries simultaneously. Thus, monitoring can be either accomplished remotely instead of through physical contacts.

In one possible example, if nine (9) batteries need to be monitored, a three-by-three switchboard matrix with a wiring harness connecting each electrolyte level detector could be assembled. A two-way circuit, which allows each detector to be selected via the switch matrix, would result in a red or green light indication for each battery. If the color is red, water, is needed, and if it is green, then no action is required.

In another embodiment, a single transducer positioned on one side of the battery could perform the same task as the receiver and transmitter discussed hereinbefore, but with a less accuracy. In such a design, a return signal would be a reverberation. To produce reverberation, an insulated metal plate might be positioned opposite the transducer on the other side of the battery. The frequency speed concept leads to the same results, but as mentioned, the accuracy is degraded.

Many additional changes in the details, components, steps, and organization of the system, herein described and illustrated to explain the nature of the invention, may be made by those skilled in the art within the principle and scope of the invention. It is therefore understood that within the scope of the appended claims, the invention may be practiced otherwise than as specifically described.

What is claimed is:

1. An apparatus used with a battery to check a level of electrolyte in regard to the battery in a non-intrusive manner to the electrolyte, said apparatus comprising:
   a battery electrolyte level detector including a frame in which said level detector crosses a pilot cell of the battery when in a final mounted position;
   a first micrometer pivotally mounted to and capable of sliding along said frame;
   a transmitter rod with an attached acoustic transmitter, said transmitter rod mounted to and capable of sliding with respect to said first micrometer;
   a second micrometer pivotally mounted to said frame;
   a receiver rod with an attached acoustic receiver, said receiver rod mounted to and capable of sliding with respect to said second micrometer;
   electronic receiver circuitry having a first band pass filter and a second band pass filter electrically connected to said acoustic receiver, with said first band pass filter used for passing an electrical signal indicative of a level of electrolyte within the battery, and said second band pass filter used for passing an electrical signal indicative of a level of electrolyte within the battery;
   an acoustic transmitter director for said acoustic transmitter with said acoustic transmitter director formed from a first transmitter cup positioned to contact said transmitter rod and formed from a second transmitter cup connected adjacent to said first transmitter cup and positioned to contact said transmitter rod;
   an acoustic receiver director for said acoustic receiver with said acoustic receiver director formed from a first receiver cup positioned to contact said receiver rod and formed from a second receiver cup connected adjacent to said first receiver cup with said second receiver cup positioned to contact said receiver rod;
   an adjustment arm connected to said transmitter rod at a first section of said arm and to said receiver rod at a second section of said arm with said adjustment arm capable of movement of said transmitter rod and said receiver rod;
   wherein said first micrometer and said second micrometer may slide along said frame with respect to each other;
   wherein said first micrometer operates to measure a distance in relation to said second micrometer for assisting placement of said acoustic transmitter by way of said transmitter rod such that said acoustic transmitter can transmit an acoustic signal through a casing of the battery on a first side of the casing opposite a second side of the casing containing the electrolyte with said acoustic transmitter adjacent to a desired level of electrolyte within the battery in a non-intrusive manner in regard to the electrolyte;
   wherein said second micrometer operates to measure a distance in relation to said first micrometer for assisting placement of said acoustic receiver by way of said receiver rod such that said acoustic receiver can receive the acoustic signal through the casing of the battery on a third side of the casing opposite a fourth side of the casing containing the electrolyte with the electrolyte contained between the second and fourth sides of the casing with said receiver adjacent to the desired level of electrolyte within the battery in a non-intrusive manner in regard to the electrolyte;
   wherein said acoustic transmitter director and said acoustic receiver director are comprised of plastic material; and
   wherein said first and second transmitter cups and said first and second receiver cups are sealed and filled with acoustically conductive jelly.

* * * * *